United States Patent [19]

Traitler et al.

[11] Patent Number: 4,776,984
[45] Date of Patent: Oct. 11, 1988

[54] PROCESS FOR THE ENRICHMENT WITH Δ6 FATTY ACIDS OF A MIXTURE OF FATTY ACIDS

[75] Inventors: Helmut Traitler, Vevey; Alfred Studer, Corseaux, both of Switzerland

[73] Assignee: Nestec S. A., Vevey, Switzerland

[21] Appl. No.: 18,778

[22] Filed: Feb. 27, 1987

Related U.S. Application Data

[63] Continuation of Ser. No. 774,896, Sep. 11, 1985, abandoned.

[30] Foreign Application Priority Data

Oct. 10, 1984 [CH] Switzerland .................. 4858/84

[51] Int. Cl.$^4$ .................. C09F 5/02; C09F 5/10; C11C 1/04
[52] U.S. Cl. .................. 260/412.2; 260/419; 260/420
[58] Field of Search .................. 260/412.2, 419, 420

[56] References Cited

U.S. PATENT DOCUMENTS 2,662,879 12/1953 Foster et al. .................. 260/96.5

FOREIGN PATENT DOCUMENTS 1603383 4/1971 France .
1240513 7/1971 United Kingdom .
2084172 7/1982 United Kingdom .

OTHER PUBLICATIONS

Markley, *Fatty Acids–Part 3*, 2nd Edition, pp. 2309–2358, (1964).
Traitler et al., CA 102:59384f (1985), *Lipids*, 1984, 19(12), pp. 923–928.
"Interêt D'une Nouvelle Plante Oleagineuse: L'Onarge (Oenothera biennis ou Larmaekiana) Apport en Acide Gamma–Linolenique et Troubles de la Desaturation en Pathologie", *Med. et Nut.*, 1985, T. XXI–No. 2, Paccalin, et al, pp. 132–136.
*Progress in the Chemistry of Fats and Other Lipids*, "Preparation of Polyunsaturated Fatty Acids from Natural Sources", Privett, vol. IX, pp. 409–452, (1968).

Primary Examiner—Charles F. Warren
Assistant Examiner—Elizabeth A. Hanley
Attorney, Agent, or Firm—Vogt & O'Donnell

[57] ABSTRACT

For the selective enrichment with fatty acids, of which the first double bond is in the 6 position, of a starting material containing fatty acids of which the first double bond is in the 6 or 9 position, the starting material is treated with a saturated solution of urea in methanol with predetermined ratios of fatty acids to urea so as to separate the fatty acids, other than the Δ6 polyunsaturated fatty acids in the form of an insoluble inclusion complex.

The enriched fractions obtained may be treated by high-performance liquid chromatography to isolate substantially pure γ-linolenic acid.

The enriched fractions, optionally recombined with glycerol, may be used in medicaments and in nutritive compositions or may even serve as starting product in the synthesis of dihomo-γ-linolenic acid.

15 Claims, No Drawings

PROCESS FOR THE ENRICHMENT WITH Δ6 FATTY ACIDS OF A MIXTURE OF FATTY ACIDS

This is a continuation application of co-pending application Ser. No. 774,896, filed 9/11/85, now abandoned.

This invention relates to the selective enrichment with polyunsaturated fatty acids, of which the first double bond is in the 6 position, more especially with γ-linolenic acid, of a mixture containing polyunsaturated fatty acids of which the first double bond is in the 6 or 9 position.

The biological importance of γ-linolenic acid (6,9,12-octadecatrienoic acid (Δ6,ω6)) is well known. It is an essential intermediate in the metabolic process which takes place in a living organism from linoleic acid (9,12-octadecadienoic acid (Δ9;ω6)) and which leads by way of dihomo-γ-linolenic acid (5,8,11-eicosatrienoic acid) to arachidonic acid (5,8,11,14-eicosatetraenoic acid). This property is utilized in its numerous dietetic, cosmetic and pharmaceutical applications. It is also known that α-linolenic acid (9,12,15-octadecatrienoic acid (Δ9,ω3)) does not participate in this metabolic process in the same way.

The majority of vegetable oils contain the Δ9 polyunsaturated acids, linoleic acid (ω6) and α-linolenic acid (ω3). A very interesting source of the Δ6 polyunsaturated aicd, γ-linolenic acid (ω6), is in the seeds of fruit of the genus Ribes, particularly black currant. The seed oil of this fruit contains appreciable quantities of Δ9 polyunsaturated acids in the form of linoleic acid (ω6) and α-linolenic acid (ω3). By way of illustration, the seed oil of this fruit consists of triglycerides of the following fatty acids in percent by weight:

| Fatty acids | Black currant | Red currant | Gooseberry |
|---|---|---|---|
| C16:0 | 6–7 | 4–5 | 7–8 |
| C18:0 | 1–2 | 1–2 | 1 |
| C18:1 cis | 9–10 | 14–15 | 15–16 |
| C18:1 trans | 0.5 | 0.5–1 | 1–2 |
| C18:2,Δ9,12 | 47–49 | 41–42 | 39–41 |
| C18:3,Δ6,9,12 | 15–19 | 4–5 | 10–12 |
| C18:3,Δ9,12,15 | 12–14 | 29–31 | 19–20 |
| C18:4,Δ6,9,12,15, | 3–4 | 2.5–3.5 | 4–5 |

For certain applications, particularly pharmaceutical applications, it is desirable to enrich the mixture of fatty acids emanating from these oils selectively with Δ6 polyunsaturated acids, particularly with γ-linolenic acid. Now, the conventional method of fractionating fatty acids by high-performance liquid chromatography (HPLC) does not enable γ-linolenic acid to be separated from α-linolenic acid.

We have surprisingly found that these two isomers may be separated by a simple method hitherto used for separating fatty acids having different degrees of saturation. In particular, the separation of unsaturated fatty acids from saturated fatty acids is described, for example, in French Patent Specification No. 1,603,383, corresponding to Great Britain Patent Specification No. 1,240,513, which relates to the enrichment with γ-linolenic acid of a mixture of fatty acids emanating from the oil of the evening primrose (Oenothera) which, moreover, contains hardly any α-linolenic acid.

The process according to the present invention is characterized in that the mixture is treated with urea dissolved in a lower alkanol in a ratio by weight of fatty acids other than the Δ6 polyunsaturates to urea of from 1:2.0 to 1:4.5, in that the insoluble inclusion complex formed is separated and in that a fraction enriched with Δ6 polyunsaturated fatty acids, particularly with γ-linolenic acid, is collected in the liquid phase.

The process is preferably carried out using a mixture of fatty acids obtained by saponification of a starting material containing seed oil of fruit of the genus Ribes, preferably oil of black currant (Ribes nigrum). Thus, it is possible to saponify the crude or refined oil or, alternatively, directly to treat the seeds, preferably converted into flake form. Saponification is carried out conventionally by treating the starting material with a concentrated strong base, for example sodium hydroxide, preferably in hot aqueous-alcoholic medium, advantageously containing a sequestering agent for metal ions, such as for example disodium ethylene diamine tetraacetate, separating the unsponifiables with a solvent, for example hexane, and neutralizing the aqueous phase, for example with hydrochloric acid in concentrated aqueous solution. After saponification, the mixture obtained is preferably protected against oxidation by addition of an antioxidant, for example 100 to 600 ppm (parts per million) of propyl gallate or, preferably, 200 to 400 ppm of ascorbyl palmitate.

The soaps obtained during neutralization of the crude oil during refining may also be used as starting product.

The fractionation is carried out under conditions which promote the selective formation of a complex of fatty acids other than Δ6 with urea in a medium in which the urea is soluble, but in which the inclusion complexes formed are not soluble. A suitable medium is a lower alkanol, for example an alkanol containing from 1 to 4 carbon atoms, preferably ethanol or methanol, methanol being particularly suitable by virtue of its high dissolving power on urea. The solution is preferably saturated and should contain from 45 to 50% by weight of urea. The saturated solution is advantageously prepared by dissolving the urea in the methanol, for example at around 60° C., while stirring until a transparent solution is obtained.

The quantity of urea is proportional to the total quantity of fatty acids to be eliminated from the mixture. When the mixture of fatty acids emanates from the saponification of the starting material mentioned above, a ratio by weight of starting material to urea of preferably about 1:3 is used. The quantity of methanol used is advantageously from 2 to 6 times and preferably about 3 times the quantity by weight of starting material used. After vigorous stirring of the mixture, it is cooled to a temperature of from 0° to 12° C. and preferably to a temperature of from 4° to 6° C. over a period of from 10 to 20 h. After separation of the precipitate, for example by centrifuging, the unreacted urea is neutralized by treating the solution with an acid, for example with preferably concentrated hydrochloric acid in aqueous solution, and the fatty acids are extracted with a solvent, preferably hexane, which is then eliminated, preferably by evaporation in vacuo.

In one preferred embodiment, the fraction enriched as described above is treated once more with urea in a ratio by weight of total fatty acids to urea of from 1:1.4 to 1:1.6. This gives a fraction containing from 92 to 96% by weight of Δ6 polyunsaturated fatty acids of which from 77 to 81% consist of γ-linolenic acid.

If desired, substantially pure γ-linolenic acid may be prepared from the fraction emanating from the second fractionation with urea by reverse high-performance liquid chromatography which enables the γ-linolenic acid to be separated from stearidonic acid (C18:4,Δ6,9,12,15).

Alternatively, a mixture containing the fatty acids enamating from saponification may be separated by chromatography and then fractionated with urea as described in the foregoing.

The free fatty acid fractions obtained in accordance with the invention may be used as such or in the form of an oil obtained by recombination with glycerol for any of the various applications of γ-linolenic acid, for example in the nutritive compositions or the medicaments described in published European Patent Applications Nos. 92,085 (corresponding to Great Britain Patent Application No. 2,118,567) and 92,076 (corresponding to U.S. Pat. No. 4,526,793) and administered orally, enterally, parenterally or topically.

The fractions recombined with glycerol in the form of an oil are particularly suitable for topical application in dermatology and in cosmeto-dermatology. The fractions containing the substantially pure γ-linolenic acid may also be used as starting product in the synthesis of dihomo-γ-linolenic acid.

The invention is illustrated by the following Examples in which the percentages and parts are by weight, unless otherwise indicated.

EXAMPLE 1

To 30 kg of refined and deodorized black currant oil are added 63.9 kg of a 14.2% aqueous-ethanolic solution of sodium hydroxide containing 95 g of disodium ethylene diamine tetraacetate. The mixture is heated to 60° C. and is then stirred at that temperature for 30 minutes. 12 kg of water are then added and the solution is cooled to 30° C.

After addition of 79 kg of hexane and stirring for 1 hour at 30° C., the mixture is left for 15 minutes to separate and the upper phase containing the unsaponifiables is eliminated. 30 kg of 32% aqueous hydrochloric acid are then added to the lower phase with stirring (to pH 1), ensuring that the temperature does not exceed 30° C. After decantation, the lower phase is eliminated and the upper phase is concentrated in a water-jet vacuum pump at 40° C.

The 28.5 kg of the fatty acid mixture obtained is added with continuous stirring to a saturated, clear solution of 90 kg of urea in 190 kg of methanol at 60° C. The mixture is cooled to 5° C. and kept at that temperature for 15 h. The solid phase formed is then separated by centrifuging whilst the liquid phase is left standing for 4 h at 5° C. The liquid phase is again separated from the solid phase by centrifuging. 180 kg of liquid phase are thus collected. 45.9 kg of hexane, 39.9 kg of a 32% aqueous hydrochloric acid solution and 106 kg of water are then added to the liquid phase and the mixture is heated to 30° C. After stirring for 1 h at 30° C., the mixture is left standing for 10 mins., after which the upper phase is collected by decantation. The lower phase is then extracted with 12 kg of hexane while stirring for 15 minutes at 30° C. The mixture is left standing for 15 mins., after which the upper phase is collected by decantation and combined with the preceding upper phase.

50 kg of water are then vigorously mixed with the combined phases. The mixture is then left standing for 3 h at ambient temperature and the upper phase containing the fatty acids is separated and dried at 40° C. by evaporation in a water-jet vacuum pump. 6.82 kg of fatty acids are thus obtained (yield 22.7%, based on the oil used). The mixture has the following composition by weight, as determined by gas chromatography:

|  | % |
| --- | --- |
| C18:1 | 0.6 |
| C18:2,Δ9,12 | 22.1 |
| C18:3,Δ6,9,12 | 55.6 |
| C18:3,Δ9,12,15 | 10.7 |
| C18:4,Δ6,9,12,15 | 11.0 |

COMPARISON EXAMPLE

The fatty acids from black currant oil used in the previous Example are fractionated by preparative high-performance liquid chromatography in the form of their methyl esters using reverse-phase RP-18 columns.

The elution of a sample having a concentration of 20% in the following solvent mixture: 67.5% methanol/22.5% ethanol/10% water, at a rate of 150 ml/min. gives the following fractions:

(1) a first fraction representing 7.6% of the mixture and containing 52% of stearidonic acid, C18:4,Δ6,9,12,15;

(2) a second fraction representing 25.4% of the mixture and containing 41% of α-linolenic acid, C18:3,Δ9,12,15 and 43% of γ-linolenic acid, C18:3,Δ6,9,12;

(3) a third fraction representing 45.8% of the mixture and containing 87% of linoleic acid, C18:2,Δ9,12; and (4) a fourth fraction representing 21.2% of the mixture and containing 85% of saturated fatty acids.

Comparison of the ratios between the quantities of γ-linolenic acid and α-linolenic acid calculated for the mixture obtained in accordance with Example 1, for fraction (2) of the Comparison Example and for black currant oil provides an indication of the selectivity of the enrichment process according to the invention:

|  | Mixture of Example 1 | Black currant oil | Fraction (2) above |
| --- | --- | --- | --- |
| % γ-linolenic acid / % α-linolenic acid | 5.2 | 1.3 | 1.1 |

It can be seen from the values indicated above that, contrary to the process according to the invention, the conventional method of chromatography does not enable the γ- and α-linolenic acids to be separated from a mixture containing them, so that the mixture cannot be enriched with γ-linolenic acid.

EXAMPLE 2

A mixture of 10.2 kg of urea and 21.5 kg of methanol is heated to 60° C. until a saturated, clear solution is obtained. The 6.82 kg of fatty acid mixture emanating from the fractionation according to Example 1 are then added with stirring to that solution. The mixture is then cooled to 5° C. and left standing at that temperature for 15 h. The solid phase formed is then separated by centrifuging whilst the liquid phase is left standing for 4 h at 5° C. The liquid phase is then centrifuged again and the crystals formed are eliminated.

5.9 kg of hexane, 5.1 kg of a 32% aqueous hydrochloric acid solution and 13.5 kg of water are then added to 23 kg of the solution obtained. The mixture heated to 30° C. is then vigorously stirred for 15 minutes. It is then left standing for 10 mins. to separate and the upper phase containing the fatty acids is separated off. 3 kg of hexane are then added to the lower phase and the mixture is vigorously stirred for 15 mins. The mixture is then left standing for 15 mins, after which the upper phase is collected by decantation and combined with the preceding upper phase.

The combined phases are then mixed with 30 kg of water while stirring for 15 mins. The mixture is left standing for 3 h, after which the lower phase is eliminated by decantation and the upper phase is collected and dried by evaporation at 40° C., in a water-jet vacuum pump. 400 ppm (parts per million) of ascorbyl palmitate are then added to the 4.05 kg of fatty acid mixture obtained (yield 13.5%, based on the mixture of fatty acids used).

The fatty acid mixture obtained has the following composition by weight, as determined by gas chromatography:

|  | % |
|---|---|
| $C18:2,\Delta9,12$ | 2.5 |
| $C18:3,\Delta6,9,12$ | 78.6 |
| $C18:3,\Delta9,12,15$ | 2.3 |
| $C18:4,\Delta6,9,12,15$ | 16.6 |

EXAMPLE 3

Black currant seeds are converted into flakes. To 35 kg of these flakes are added 150 kg of a 14.2% aqueous-ethanolic solution of sodium hydroxide containing 223 g of disodium ethylene diamine tetraacetate, the suspension heated to 60° C. is stirred for 1 hour and the residue formed is separated by filtration in vacuo. The filter is then rinsed and washed with a quantity of ethanol equal to the weight of the flakes used, after which the majority of the ethanol is evaporated in the form of an azeotropic mixture. A 32% aqueous hydrochloric acid solution is then added to the residue until a pH of 1 is obtained.

After decantation, the majority of the fatty acids are separated in the form of the upper organic phase formed. 35 kg of hexane are added to the lower aqueous phase which is then decanted again. The lower phase is washed a second time with 35 kg of hexane. The combined organic phases (comprising the fatty acids and the two solutions in hexane) are then washed twice with 70 kg of water and the solvent is evaporated at 40° C. in a water-jet vacuum pump. The residue represents 6.72 kg of a mixture of fatty acids of which the composition as determined by gas chromatography is identical with that of the mixture obtained by saponification of the oil used in Example 1. The mixture is then subjected to fractionation under the conditions of Example 1.

EXAMPLE 4

A 20% solution of the mixture of fatty acids emanating from the double fractionation of Example 2 is prepared in the following solvent mixture: 67.5% methanol/22.5% ethanol/10% water.

10 ml of this solution are then injected into a preparative high-performance liquid chromatography apparatus provided with reverse-phase RP-18 silica gel columns. The above solvent mixture is used as the mobile phase at a rate of 100 ml/min. and the quantitative identification is carried out with a refractive index detector.

The two principal fatty acids ($\gamma$-linolenic and stearidonic) of the mixture obtained in accordance with Example 2 (78.6% $\gamma$-linolenic acid, 16.6% stearidonic acid) are effectively separable by the above method, the two eluted fractions obtained having the following compositions:

|  |  | % |
|---|---|---|
| first fraction: | $C18:3,\Delta6,9,12$ | 49 |
| (representing 20% of the mixture) | $C18:4,\Delta6,9,12,15$ | 51 |
| second fraction: | $C18:3,\Delta6,9,12$ | 96 |
| (representing 80% of the mixture) | $C18:3,\Delta9,12,15$ | 2.5 |
|  | $C18:4,\Delta6,12,15$ | 1.5 |

The second fraction may advantageously serve as starting product in the synthesis of dihomo-$\gamma$-linolenic acid.

EXAMPLE 5

100 g of the fatty acid mixtures obtained in accordance with Examples 1 to 4 are reacted with 15 g of glycerol for 5 h at 210° C. under a pressure of 5 mm Hg. 96 g of triglycerides are thus obtained in a yield of 92%. The oils obtained are suitable for dermatological and cosmeto-dermatological applications.

We claim:

1. A process comprising treating polyunsaturated fatty acids, obtained from seeds of the fruit of the genus Ribes, with urea dissolved in a lower alkanol, in a ratio by weight of fatty acids other than delta 6 polyunsaturated fatty acids to urea of from 1:2.0 to 1:4.5, thereby forming a liquid phase fraction and an insoluble inclusion complex, separating the insoluble inclusion complex from the liquid phase fraction and extracting and collecting fatty acids from the liquid phase fraction.

2. A process as claimed in claim 1 further comprising treating the collected fatty acids with urea dissolved in a lower alkanol, in a ratio by weight of total fatty acids to urea of from approximately 1:1.4 to 1:1.6, thereby forming a second liquid phase fraction and a second insoluble inclusion complex, separating the second insoluble inclusion complex from the second liquid phase fraction and extracting and collecting fatty acids from the second liquid phase fraction.

3. A process as claimed in claim 2 further comprising treating the fatty acids collected from the second liquid phase fraction by reverse-phase high-performance liquid chromatography to separate gamma-linolenic acid from stearidonic acid and collecting the gamma-linolenic acid.

4. A process for obtaining gamma-linolenic acid from polyunsaturated fatty acids derived from seeds of fruit of the genus Ribes comprising:
   (a) treating the fatty acids with urea dissolved in a lower alkanol, in a ratio by weight of fatty acids other than delta 6 polyunsaturated fatty acids to urea of from 1:2.0 to 1:4.5, thereby forming a liquid phase fraction and an insoluble inclusion complex;
   (b) separating the inclusion complex from the liquid phase fraction and extracting and collecting fatty acids from the liquid phase fraction;
   (c) treating the collected fatty acids with urea, in a ratio of total fatty acids to urea of from approximately 1:1.4 to 1:1.6, thereby forming a second liquid phase fraction and a second insoluble inclusion complex;

(d) separating the second inclusion complex from the second liquid phase fraction and extracting and collecting fatty acids from the second liquid phase fraction; and (e) subjecting the fatty acids collected from the second liquid phase fraction to reverse-phase high-performance liquid chromatography to separate gamma-linolenic acid from stearidonic acid and collecting the gamma-linolenic acid.

5. A process as claimed in claim 1 further comprising esterifying the collected fatty acids with glycerol.

6. A process as claimed in claim 2 further comprising esterifying the fatty acids collected from the second liquid phase fraction with glycerol.

7. A process as claimed in claim 3 or 4 further comprising esterifying the collected gamma-linolenic acid with glycerol.

8. A process as claimed in claim 3 or 4 further comprising converting the collected gamma-linolenic acid to dihomo-gamma-linolenic acid.

9. A process as claimed in claim 1 or 4 further comprising obtaining the fatty acids to be treated by saponifying oil of the seeds.

10. A process as claimed in claim 9 wherein the ratio by weight of fatty acids, other than delta 6 fatty acids, to urea is approximately 1:3.

11. A process as claimed in claim 9 further comprising subjecting the fatty acids obtained by saponification to chromatography to obtain a fatty acid fraction containing gamma-linolenic acid and then treating the fraction with urea.

12. A process as claimed in claim 1 or 2 or 4 wherein the urea dissolved in the alkanol is in the form of a saturated solution.

13. A process as claimed in claim 11 wherein the alkanol is selected from the group consisting of methanol and ethanol and contains from 45 to 50% by weight of urea.

14. A process as claimed in claim 1 or 2 or 4 wherein the fatty acids are extracted and collected from the liquid phase fraction by a solvent which is then eliminated from the fatty acids.

15. A process as claimed in claim 14 wherein the solvent is hexane which is eliminated by evaporation.

* * * * *

UNITED STATES PATENT AND TRADEMARK OFFICE
CERTIFICATE OF CORRECTION

PATENT NO. : 4,776,984

DATED : October 11, 1988

INVENTOR(S) : Helmut TRAITLER, et al.

It is certified that error appears in the above-identified patent and that said Letters Patent is hereby corrected as shown below:

Column 1, line 6, insert --06/-- before "774,896".

Column 1, line 17, ";" should be --,--.

Column 6, line 16, "C18:4,$\Delta$6,12,15" should be --C18:4,$\Delta$6,9,12,15--.

Signed and Sealed this

Twenty-eighth Day of March, 1989

Attest:

DONALD J. QUIGG

*Attesting Officer*   *Commissioner of Patents and Trademarks*